(12) United States Patent
Bojarski et al.

(10) Patent No.: US 8,650,042 B2
(45) Date of Patent: Feb. 11, 2014

(54) CASE AND MEDICATION TRACKING

(75) Inventors: Karen Bojarski, Butler, PA (US); Preeti Churbock, Pittsburgh, PA (US)

(73) Assignee: McKesson Automation Inc.

( * ) Notice: Subject to any disclaimer, the term of this patent is extended or adjusted under 35 U.S.C. 154(b) by 0 days.

(21) Appl. No.: 13/250,035

(22) Filed: Sep. 30, 2011

(65) Prior Publication Data
US 2013/0085766 A1   Apr. 4, 2013

(51) Int. Cl.
*G06Q 50/00* (2012.01)

(52) U.S. Cl.
USPC .................................. 705/2; 705/3

(58) Field of Classification Search
USPC ........................................ 705/2–3
See application file for complete search history.

(56) References Cited

U.S. PATENT DOCUMENTS

| | | | |
|---|---|---|---|
| 4,717,042 A | 1/1988 | McLaughlin | |
| 4,785,969 A | 11/1988 | McLaughlin | |
| 4,847,764 A | 7/1989 | Halvorson | |
| 5,014,875 A | 5/1991 | McLaughlin et al. | |
| 5,190,185 A | 3/1993 | Blechl | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,438,523 A * | 8/1995 | Humm et al. | 700/243 |
| 5,460,294 A * | 10/1995 | Williams | 221/2 |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A | 1/1997 | McDonald et al. | |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,797,515 A | 8/1998 | Liff et al. | |
| 5,805,456 A | 9/1998 | Higham et al. | |
| 5,820,237 A * | 10/1998 | Robey | 312/268 |
| 5,842,976 A | 12/1998 | Williamson | |
| 5,878,885 A | 3/1999 | Wangu et al. | |
| 5,880,443 A | 3/1999 | McDonald et al. | |
| 5,883,806 A | 3/1999 | Meador et al. | |
| 5,893,697 A | 4/1999 | Zini et al. | |
| 5,905,653 A | 5/1999 | Higham et al. | |
| 5,912,818 A | 6/1999 | McGrady et al. | |
| 5,927,540 A | 7/1999 | Godlewski | |
| 5,940,306 A | 8/1999 | Gardner et al. | |
| 5,971,593 A | 10/1999 | McGrady | |
| 6,003,006 A | 12/1999 | Colella et al. | |
| 6,011,999 A | 1/2000 | Holmes | |
| 6,021,392 A | 2/2000 | Lester et al. | |
| 6,039,467 A | 3/2000 | Holmes | |
| 6,065,819 A | 5/2000 | Holmes et al. | |
| 6,068,156 A | 5/2000 | Liff et al. | |
| 6,109,774 A | 8/2000 | Holmes et al. | |

(Continued)

*Primary Examiner* — Sind Phongsvirajati
(74) *Attorney, Agent, or Firm* — Alston & Bird LLP (57) ABSTRACT

Systems, methods, apparatus, and computer program products are provided for medication management. In one embodiment, a medication dispense queue can be created for a medical procedure to pre-stock a medication dispensing unit prior to the medical procedure. Then, the medications can be tracked to determine when a medication has been, for example, dispensed, administered, wasted, and/or returned.

15 Claims, 7 Drawing Sheets

(56) References Cited

U.S. PATENT DOCUMENTS

| | | | | |
|---|---|---|---|---|
| 6,112,502 | A | 9/2000 | Frederick et al. | |
| 6,116,461 | A | 9/2000 | Broadfield et al. | |
| 6,151,536 | A | 11/2000 | Arnold et al. | |
| 6,170,230 | B1 | 1/2001 | Chudy et al. | |
| 6,176,392 | B1 | 1/2001 | William et al. | |
| 6,189,727 | B1 | 2/2001 | Shoenfeld | |
| 6,223,934 | B1 | 5/2001 | Shoenfeld | |
| 6,256,967 | B1 | 7/2001 | Hebron et al. | |
| 6,283,322 | B1 | 9/2001 | Liff et al. | |
| 6,289,656 | B1 | 9/2001 | Wangu et al. | |
| 6,338,007 | B1 | 1/2002 | Broadfield et al. | |
| 6,339,732 | B1 | 1/2002 | Phoon et al. | |
| 6,361,263 | B1 | 3/2002 | Dewey et al. | |
| 6,370,841 | B1 | 4/2002 | Chudy et al. | |
| 6,449,927 | B2 | 9/2002 | Hebron et al. | |
| 6,471,089 | B2 | 10/2002 | Liff et al. | |
| 6,497,342 | B2 | 12/2002 | Zhang et al. | |
| 6,499,270 | B2 | 12/2002 | Peroni et al. | |
| 6,532,399 | B2 | 3/2003 | Mase | |
| 6,564,121 | B1 | 5/2003 | Wallace et al. | |
| 6,581,798 | B2 | 6/2003 | Liff et al. | |
| 6,604,019 | B2 * | 8/2003 | Ahlin et al. | 700/231 |
| 6,609,047 | B1 | 8/2003 | Lipps | |
| 6,611,733 | B1 | 8/2003 | De La Huerga | |
| 6,625,952 | B1 | 9/2003 | Chudy et al. | |
| 6,636,780 | B1 * | 10/2003 | Haitin et al. | 700/236 |
| 6,640,159 | B2 | 10/2003 | Holmes et al. | |
| 6,650,964 | B2 | 11/2003 | Spano, Jr. et al. | |
| 6,671,579 | B2 | 12/2003 | Spano, Jr. et al. | |
| 6,681,149 | B2 | 1/2004 | William et al. | |
| 6,729,482 | B1 * | 5/2004 | Hovik | 211/121 |
| 6,742,671 | B2 | 6/2004 | Hebron et al. | |
| 6,755,931 | B2 | 6/2004 | Vollm et al. | |
| 6,760,643 | B2 | 7/2004 | Lipps | |
| 6,775,591 | B1 * | 8/2004 | Shoenfeld | 700/243 |
| 6,776,304 | B2 | 8/2004 | Bossi et al. | |
| 6,785,589 | B2 | 8/2004 | Eggenberger et al. | |
| 6,790,198 | B1 | 9/2004 | White et al. | |
| 6,814,254 | B2 | 11/2004 | Liff et al. | |
| 6,814,255 | B2 | 11/2004 | Liff et al. | |
| 6,847,861 | B2 * | 1/2005 | Lunak et al. | 700/242 |
| 6,874,684 | B1 | 4/2005 | Denenberg et al. | |
| 6,892,780 | B2 | 5/2005 | Vollm et al. | |
| 6,895,304 | B2 | 5/2005 | Spano, Jr. et al. | |
| 6,975,922 | B2 | 12/2005 | Duncan et al. | |
| 6,985,797 | B2 | 1/2006 | Spano, Jr. et al. | |
| 6,996,455 | B2 | 2/2006 | Eggenberger et al. | |
| 7,010,389 | B2 * | 3/2006 | Lunak et al. | 700/243 |
| 7,014,063 | B2 | 3/2006 | Shows et al. | |
| 7,016,766 | B2 | 3/2006 | William et al. | |
| 7,040,504 | B2 | 5/2006 | Broadfield et al. | |
| 7,052,097 | B2 | 5/2006 | Meek, Jr. et al. | |
| 7,072,737 | B2 * | 7/2006 | Lunak et al. | 700/236 |
| 7,072,855 | B1 | 7/2006 | Godlewski et al. | |
| 7,077,286 | B2 | 7/2006 | Shows et al. | |
| 7,085,621 | B2 | 8/2006 | Spano, Jr. et al. | |
| 7,092,796 | B2 | 8/2006 | Vanderveen | |
| 7,093,755 | B2 | 8/2006 | Jordan et al. | |
| 7,100,792 | B2 | 9/2006 | Hunter et al. | |
| 7,103,419 | B2 | 9/2006 | Engleson et al. | |
| 7,111,780 | B2 | 9/2006 | Broussard et al. | |
| 7,139,639 | B2 | 11/2006 | Broussard et al. | |
| 7,140,542 | B2 * | 11/2006 | Andreasson et al. | 235/385 |
| 7,150,724 | B2 | 12/2006 | Morris et al. | |
| 7,155,306 | B2 * | 12/2006 | Haitin et al. | 700/242 |
| 7,171,277 | B2 | 1/2007 | Engleson et al. | |
| 7,194,333 | B2 * | 3/2007 | Shoenfeld | 700/243 |
| 7,218,231 | B2 | 5/2007 | Higham | |
| 7,228,198 | B2 | 6/2007 | Vollm et al. | |
| 7,232,066 | B2 * | 6/2007 | Andreasson et al. | 235/385 |
| 7,249,688 | B2 | 7/2007 | Hunter et al. | |
| 7,348,884 | B2 | 3/2008 | Higham | |
| 7,417,729 | B2 | 8/2008 | Greenwald | |
| 7,419,133 | B2 | 9/2008 | Clarke et al. | |
| 7,426,425 | B2 | 9/2008 | Meek, Jr. et al. | |
| 7,554,449 | B2 | 6/2009 | Higham | |
| 7,568,627 | B2 * | 8/2009 | Lunak et al. | 235/462.45 |
| 7,571,024 | B2 | 8/2009 | Duncan et al. | |
| 7,588,167 | B2 | 9/2009 | Hunter et al. | |
| 7,747,347 | B2 * | 6/2010 | Park, IV | 700/243 |
| 7,766,242 | B2 * | 8/2010 | Lunak et al. | 235/462.45 |
| 7,865,263 | B2 * | 1/2011 | Spano et al. | 700/237 |
| 8,009,913 | B2 * | 8/2011 | Greyshock | 382/181 |
| 8,019,470 | B2 | 9/2011 | Meek et al. | 700/237 |
| 8,027,749 | B2 * | 9/2011 | Vahlberg et al. | 700/241 |
| 8,036,773 | B2 * | 10/2011 | Braun et al. | 700/215 |
| 8,073,563 | B2 * | 12/2011 | Vahlberg et al. | 700/244 |
| 8,077,963 | B2 * | 12/2011 | Wang et al. | 382/153 |
| 8,103,379 | B2 * | 1/2012 | Biba et al. | 700/243 |
| 8,126,590 | B2 * | 2/2012 | Vahlberg et al. | 700/241 |
| 8,131,397 | B2 * | 3/2012 | Vahlberg et al. | 700/236 |
| 8,140,186 | B2 * | 3/2012 | Vahlberg et al. | 700/242 |
| 8,280,550 | B2 * | 10/2012 | Levy et al. | 700/241 |
| 2005/0149361 | A1 * | 7/2005 | Saus et al. | 705/3 |

* cited by examiner

| Dispense | Return / Waste | Manage Meds | Discrepancies (0) | | About | Log Out |
|---|---|---|---|---|---|---|
| | | | | | | Administration |

Please select a patient

| My Patients | Scheduled Patients | All Patients | ☑ Show Closed Cases | From 06/13/2011 To 06/13/2011 | | Patient Name | Enter search here | | | |
| | | | | | | Provider | All | | | |

| Patient Name | Admit Date | Patient ID | Birth Date | Medical Record # | Allergies | Time | Location | Type | Status |
|---|---|---|---|---|---|---|---|---|---|
| Doe, Jane<br>APPENDECTOMY | 06/13/2011 | 119400111 | 01/11/1940 | 119400111 | | 06:00 | OR1 | General | Started |
| Blue, IntelliShelf<br>HERNIA REPAIR | 06/12/2011 | 119400116 | 01/16/1940 | 119400116 | | 07:30 | OR2 | General | Closed |
| Blue, MedShelf | 06/10/2011 | 119400126 | 01/26/1940 | 119400126 | A | 07:45 | OR1 | General | Paused |
| | | | | | | 09:00 | ORX | | |
| Doe, Jen L.<br>COLECTOMY w/ colostomy | 06/12/2011 | 0805540032 | 01/29/1975 | 0000540563 | | 13:00 | CATH2 | | |
| | | | | | | 13:30 | ROOM 1 | General | Not Started |
| , , | | | | | | | | | |
| , , | | | | | | | | | |
| Doe, Joe L.<br>TOTAL HIP REPLACEMENT | 06/12/2011 | 119400216 | 02/16/1940 | 119400216 | | 15:30 | OR1 | General | Not Started |
| , , | | | | | | | | | |
| , , | | | | | | | | | |

| | | | | | My Stock | Admit |
|---|---|---|---|---|---|---|
| BA1 | | ■ Connected | | Manual Override | | Unlocked |

Fig. 5

| Dispense | Return / Waste | Manage Meds | Discrepancies (0) | About | Log Out |
|---|---|---|---|---|---|
| | | | | | Administration |

Open drawer to begin dispensing medications for Doe, Jane

Doe, Jane
Birth Date: 01/11/1940   Patient ID: 119400111
Allergies:

─ Medication Search ─
Enter search here

○ Generic Name
◉ Brand Name

Drawer:   Pocket:

| Drawer 1 |
| Drawer 2 |
| Drawer 3 |
| Drawer 4 |
| Drawer 5 |
| Drawer 6 |
| Drawer 7 |

| Doe, Jane x | Select Next Patient | | | | | |
|---|---|---|---|---|---|---|
| | | | | | | My Stock |
| Medication | Dispense Qty | Return Qty | Waste Qty | Admin Qty | Stock | |
| DOBUTamine 12.5MG/ML VIAL (DOBUtamine 12.5MG/ML VIAL) | 1 | | | | | |
| RINGERS SOLUTION LACTATED IV SOLN (LACTATED RINGERS INJECTION) | 1 | | | | | |
| FENTANYL CITRATE/PF 0.05MG/ML 5ML AMPUL (SUBLIMAZE 0.05MG/ML AMPUL) | 1 | | 1 ML | 0.2 MG | | |
| MEPERIDINE HCL/PF 100MG/ML AMPUL (DEMEROL 100MG/ML AMPUL) | | | | 100 MG | | |
| DOXAPRAM HCL 20MG/ML VIAL (DOPRAM 20MG/ML VIAL) | | | | | Out of Stock | |
| | | | | | | |
| | | | | | | |
| | | | | | | |

| BA1 | ■ Connected | Manual Override | Return | Waste |
|---|---|---|---|---|
| | | | | Unlocked |

FENTANYL CITRATE/PF 0.05MG/ML 5ML AMPUL INJECTION (SUBLIMAZE 0.05MG/ML AMPUL)

Waste Quantity

Administered 0.2MG (Max Waste 1ML)

| 1 | 2 | 3 |
| 4 | 5 | 6 |
| 7 | 8 | 9 |
| . | 0 | |

Clear | Backspace

Dispense | Return / Waste | Manage Meds | Discrepancies (0) | About | Log Out
Administration
Enter a quantity
BA1 | Connected | Manual Override | Waste | Skip | Cancel | Unlocked

US 8,650,042 B2

CASE AND MEDICATION TRACKING

BACKGROUND

In various embodiments, anesthesia team members typically use medication dispensing units (storing/housing various medications) in surgical/procedural areas to dispense medications and/or track the medications that have been administered. Thus, a need exists for proactively determining the medications and the corresponding quantities that need to be stocked on medication dispensing units based on the surgical procedures for which the units will be used during a specific time period. Further, during surgical procedures, anesthesia team members are often busy with patient care. Thus, the team members generally desire quick and easy access to medications without double entry of information in different systems being used. Accordingly, a need exists to simplify the process for tracking medications that have been, for example, dispensed, unused, administered, wasted, and/or returned.

BRIEF SUMMARY

In general, embodiments of the present invention provide systems, methods, apparatus, and computer program products for medication management.

In accordance with one aspect, a method for medication management is provided. In one embodiment, the method comprises (1) electronically identifying a medication list for a case associated with a patient, wherein (A) the case identifies a medical procedure to be performed for the patient and (B) the medication list (i) corresponds to the medical procedure and (ii) identifies a plurality of medications; (2) electronically receiving notification that a quantity of a first medication from the medication list was dispensed from a medication dispensing unit; (3) electronically receiving notification that a quantity of the first medication was administered to the patient; and (4) electronically determining whether a quantity of the first medication that was dispensed from the medication dispensing unit is unaccounted for based at least in part on the quantity of the first medication that was administered to the patient.

In accordance with another aspect, a computer program product for medication management is provided. The computer program product may comprise at least one computer-readable storage medium having computer-readable program code portions stored therein, the computer-readable program code portions comprising executable portions configured to (1) identify a medication list for a case associated with a patient, wherein (A) the case identifies a medical procedure to be performed for the patient and (B) the medication list (i) corresponds to the medical procedure and (ii) identifies a plurality of medications; (2) receive notification that a quantity of a first medication from the medication list was dispensed from a medication dispensing unit; (3) receive notification that a quantity of the first medication was administered to the patient; and (4) determine whether a quantity of the first medication that was dispensed from the medication dispensing unit is unaccounted for based at least in part on the quantity of the first medication that was administered to the patient.

In accordance with yet another aspect, an apparatus comprising at least one processor and at least one memory including computer program code is provided. In one embodiment, the at least one memory and the computer program code may be configured to, with the processor, cause the apparatus to at least (1) identify a medication list for a case associated with a patient, wherein (A) the case identifies a medical procedure to be performed for the patient and (B) the medication list (i) corresponds to the medical procedure and (ii) identifies a plurality of medications; (2) receive notification that a quantity of a first medication from the medication list was dispensed from a medication dispensing unit; (3) receive notification that a quantity of the first medication was administered to the patient; and (4) determine whether a quantity of the first medication that was dispensed from the medication dispensing unit is unaccounted for based at least in part on the quantity of the first medication that was administered to the patient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

I. Methods, Apparatus, Systems, and Computer Program Products

As should be appreciated, various embodiments may be implemented in various ways, including as methods, apparatus, systems, or computer program products. Accordingly, various embodiments may take the form of an entirely hardware embodiment or an embodiment in which a processor is programmed to perform certain steps. Furthermore, various implementations may take the form of a computer program product on a computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

II. Exemplary System Architecture

Figure 1:
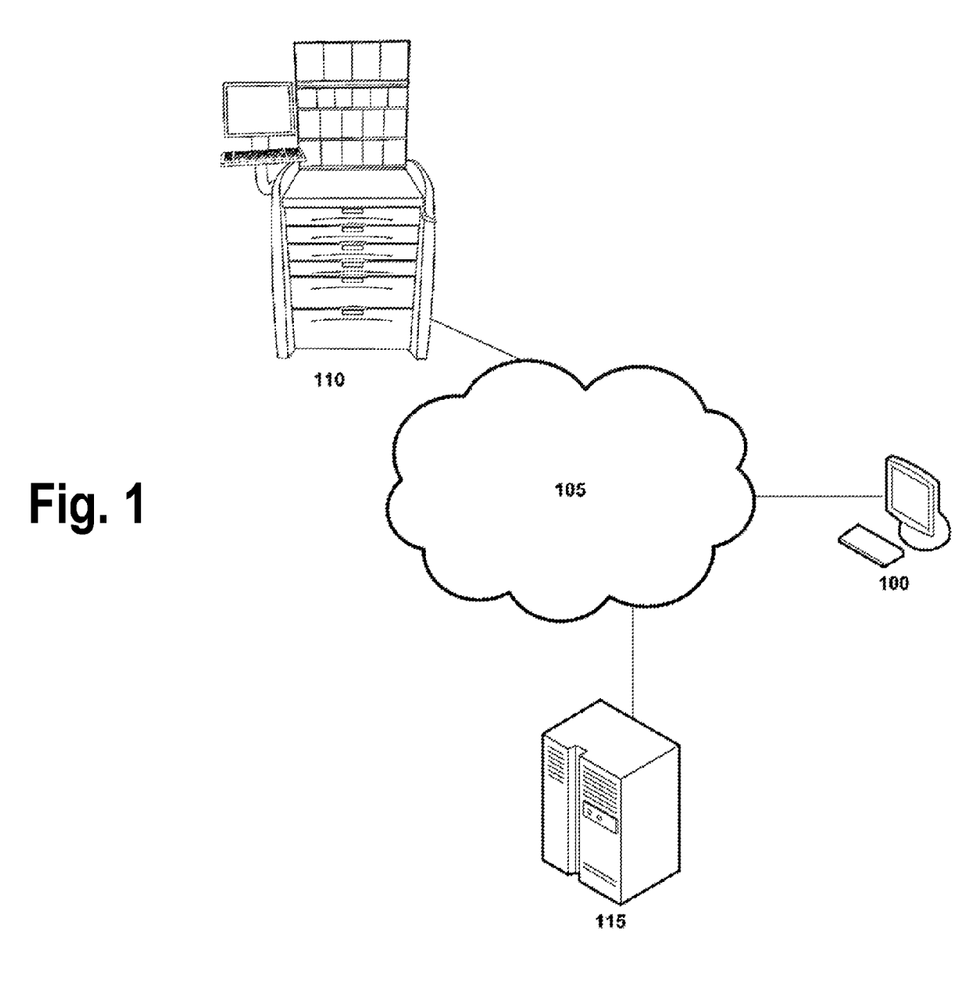
FIG. 1 is an overview of a system according to various embodiments of the present invention.
Figure 3:
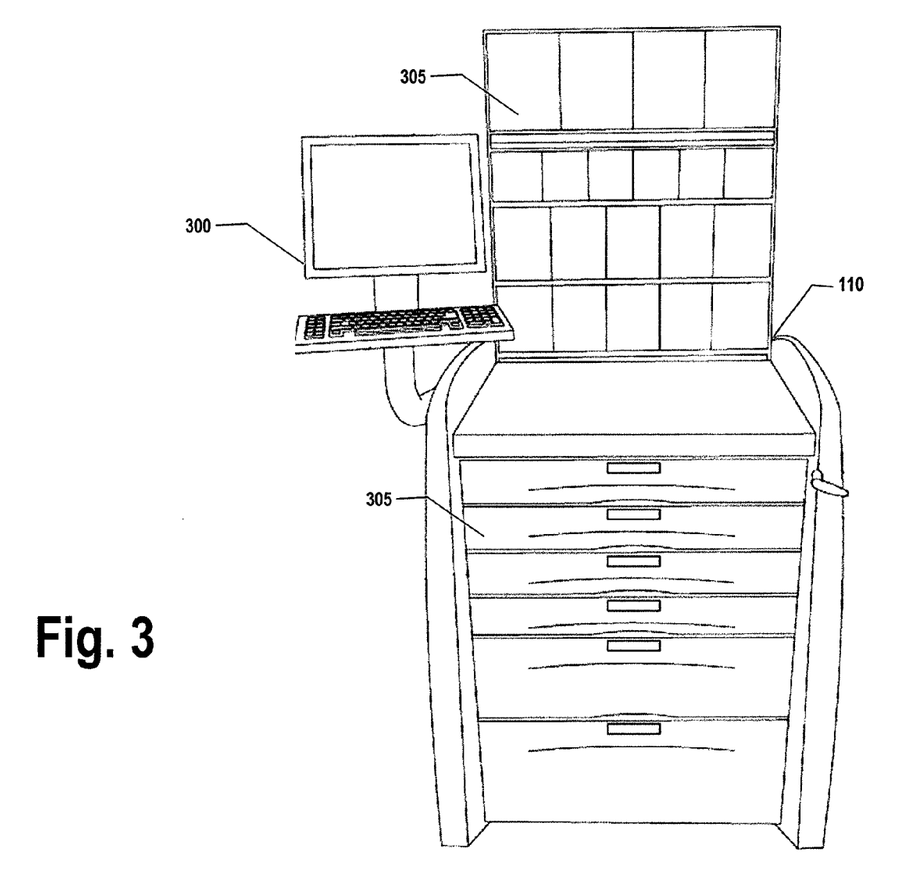
FIG. 3 illustrates a medication dispensing unit according to an exemplary embodiment of the present invention.

FIG. 1 provides an illustration of a system that can be used in conjunction with various embodiments of the present invention. As shown in FIG. 1, the system may include one or more anesthesia care computing entities 100, one or more networks 105, one or more medication dispensing units 110 (and corresponding computing entities, such as shown in FIG. 3), and one or more data storage/facilitation computing entities 115. Each of the components of the system may be in electronic communication with, for example, one another over the same or different wireless or wired networks including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

1. Exemplary Anesthesia Care Computing Entity

Figure 2:
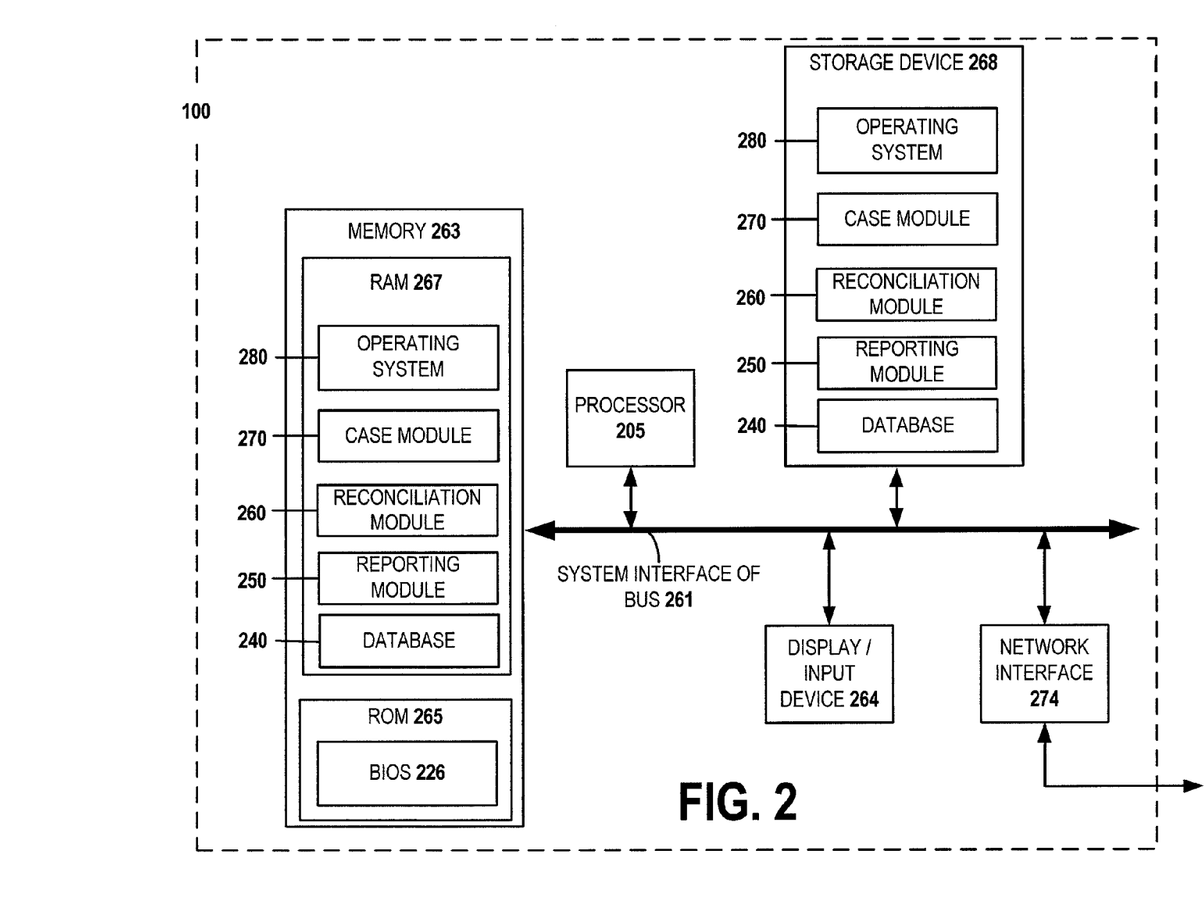
FIG. 2 is an exemplary schematic diagram of an anesthesia care computing entity according to one embodiment of the present invention.

FIG. 2 provides a schematic of an anesthesia care computing entity 100 according to one embodiment of the present invention. In general, the term "computing entity" may refer to, for example, any computer, computing device, mobile phone, desktop, tablet, notebook or laptop, distributed system, server, blade, gateway, switch, processing device, or combination of processing devices adapted to perform the functions described herein. Thus, anesthesia care computing entities 100 can be used in a medical provider's office, in surgical/procedural areas, and/or a variety of other settings. The anesthesia care computing entities 100 may include, be associated with, or be in communication with a variety of computing entities, such as medication dispensing units 110, data storage/facilitation computing entities 115, vital sign monitors, vaporizers, ventilators, pumps, and/or the like.

As will be understood from this figure, in one embodiment, the anesthesia care computing entity 100 may include a processor 205 that communicates with other elements within the anesthesia care computing entity 100 via a system interface or bus 261. The processor 205 may be embodied in a number of different ways. For example, the processor 205 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an exemplary embodiment, the processor 205 may be configured to execute instructions stored in memory or otherwise accessible to the processor 205. As such, whether configured by hardware or software methods, or by a combination thereof, the processor 205 may represent an entity capable of performing operations according to embodiments of the present invention when configured accordingly. For example, as discussed in more detail below, the anesthesia care computing entity 100 may be configured, among other things, to receive case information for patients and generate medication lists. The anesthesia care computing entity 100 care entity may also be used to track the dispensing, administration, and/or waste of medications for one or more cases. A display/input device 264 for receiving and displaying data may also be included in (or in communication with) the anesthesia care computing entity 100. This display device/input device 264 may be, for example, a keyboard or pointing device that is used in combination with a monitor (e.g., an electronic screen/display). The display/input device 264 may be a touchscreen that can detect the presence and location of a touch within the display area. The anesthesia care computing entity 100 may further include transitory and non-transitory memory 263, which may include both random access memory (RAM) 267 and read only memory (ROM) 265. The anesthesia care computing entity's ROM 265 may be used to store a basic input/output system (BIOS) 226 containing the basic routines that help to transfer information to the different elements within the anesthesia care computing entity 100.

In addition, in one embodiment, the anesthesia care computing entity 100 may include at least one storage device 268, such as a hard disk drive, a CD drive, and/or an optical disk drive for storing information on various computer-readable media. The storage device(s) 268 and its associated computer-readable media may provide nonvolatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. Additionally, each of these storage devices 268 may be connected to the system bus 261 by an appropriate interface.

Furthermore, a number of executable instructions, applications, scripts, program modules, and/or the like may be stored by the various storage devices 268 and/or within RAM 267. Such executable instructions, applications, scripts, program modules, and/or the like may include an operating system 280, a case module 270, a reconciliation module 260, and a reporting module 250. As discussed in more detail below, these executable instructions, applications, program modules, and/or the like may control certain aspects of the operation of the anesthesia care computing entity 100 with the assistance of the processor 205 and operating system 280—although their functionality need not be modularized. In addition to the program modules, the anesthesia care computing entity 100 may store or be in communication with one or more databases, such as database 240.

Also located within the anesthesia care computing entity 100, in one embodiment, is a network interface 274 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the anesthesia care computing entity 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the anesthesia care computing entity's 100 components may be located remotely from other anesthesia care computing entity 100 components. Furthermore, one or more of the components may be combined and additional components performing functions described herein may be included in the anesthesia care computing entity 100.

2. Exemplary Medication Dispensing Unit

In one embodiment, a medication dispensing unit (MDU) 110 can be used to hold/store/house various medications and/or supplies (e.g., syringes, intravenous bags). Such MDUs may be used in a variety of environments, including surgical/procedural areas. Medications in an MDU may be categorized as controlled or non-controlled. For security reasons, controlled medications may require more safeguards than non-controlled medications. For example, controlled medications may need to be kept in a locked compartment 305 (always or until moved to a controlled environment such as a surgical/procedural area). Additionally, certain procedures may require periodically accounting for the controlled medications to ensure that none have been lost or stolen. Non-controlled medications may not require as much control as controlled medications, but can also be stored in an MDU 110. Thus, depending on the setting and control required for the medications, medications may be held/stored/housed in a variety of MDUs 110. An MDU 110 may be one or more carts, one or more cabinets, one or more bins, one or more drawers, one or more storage devices, and/or various other types of storage equipment and/or devices.

FIG. 3 illustrates an exemplary MDU 110 that may be used in conjunction with embodiments of the present invention. As shown in FIG. 3, an MDU 110 may include an MDU computing entity 300 and be associated with or be in communication with a variety of other computing entities, such as anesthesia care computing entities 100, data storage/facilitation computing entities 115, vital sign monitors, vaporizers, ventilators, pumps, and/or the like. The MDU computing entity may also include components and have functionality similar to that described above with regard to the anesthesia care computing entity 100. For example, the MDU computing entity 300 may include a display screen, a keyboard, and/or other input and/or output devices, which are not shown and which may include, for example, a speaker, a barcode reader, a radio frequency identification (RED) tag reader, and the like.

The MDU computing entity 300 may be used to access and/or provide information associated with the medications and dispensing/delivery devices corresponding to the MDU 110. The MDU computing entity 300 may also be used to access and/or provide medical data regarding the parties (e.g., patients) for whom medications may be dispensed or administered from the MDU 110. For example, the MDU computing entity 300 may communicate with the anesthesia care computing entity 100 and/or data storage/facilitation computing entities 115 to request medical data regarding health care patients (and their cases), as well as provide information regarding the medications dispensed and/or administered.

3. Exemplary Data Storage/Facilitation Computing Entities

In one embodiment, the data storage/facilitation computing entity 115 may be used to store data, provide data to various entities, connect various entities (e.g., serving as a backbone), and facilitate communication with a variety of entities. The data storage/facilitation computing entity 115 may also include components and have functionality similar to that described above with regard to the anesthesia care computing entity 100. In one embodiment, the data storage/facilitation computing entity 115 may store, receive, and/or have access to medical data for patients. Medical data may be received from, for example, an electronic medical record (EMR) of a patient or from other data known about the patient from available sources, or from information provided by patients. The medical data may also include historical data from a patient's medical records. For example, the medical data may indicate a condition (and/or conditions) for which the patient is being treated. In one embodiment, the data storage/facilitation computing entity 115 may serve to facilitate the communication of such medical data to a variety of computing entities, including the anesthesia care computing entity 100, MDU computing entity 110, pharmacy entities, and/or the like.

III. Exemplary System Operation

Figure 4:
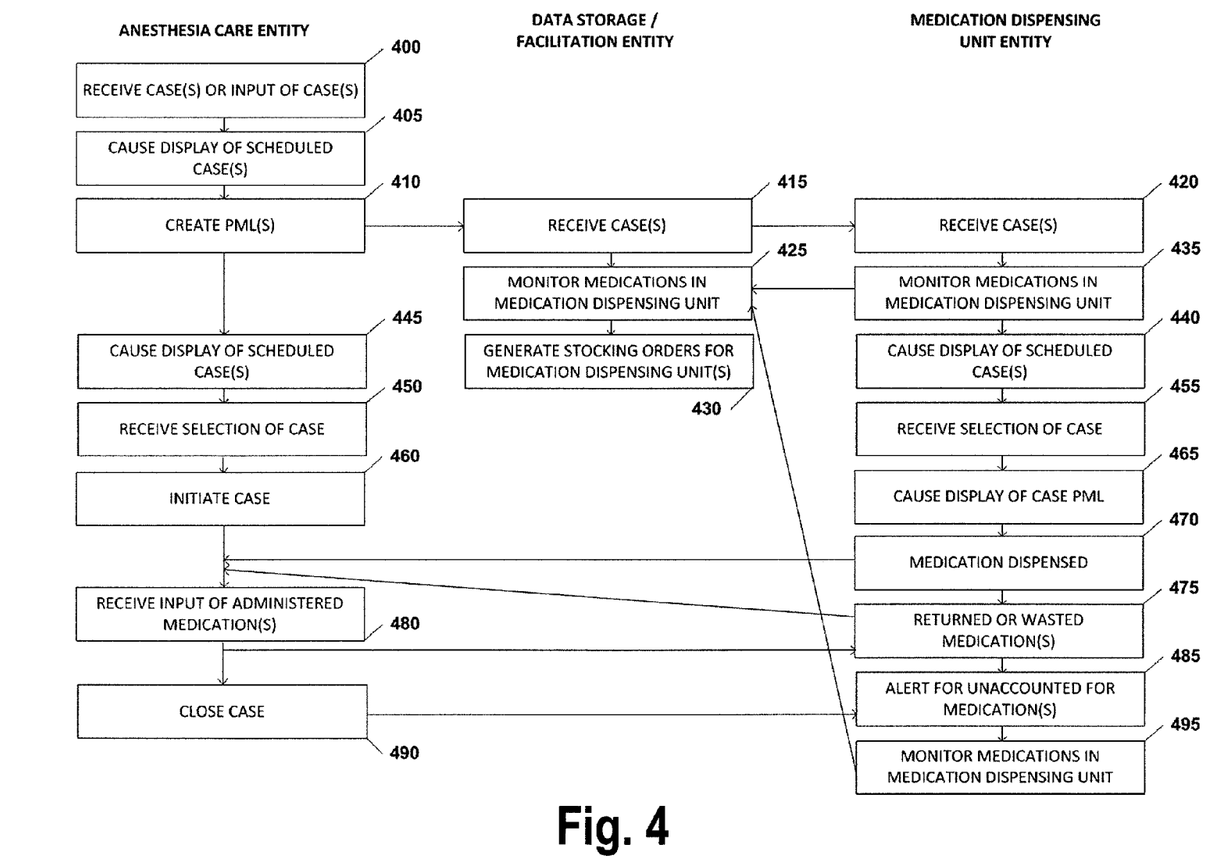
FIG. 4 is a flowchart illustrating operations and processes that can be used in accordance with various embodiments of the present invention.
Figure 5:
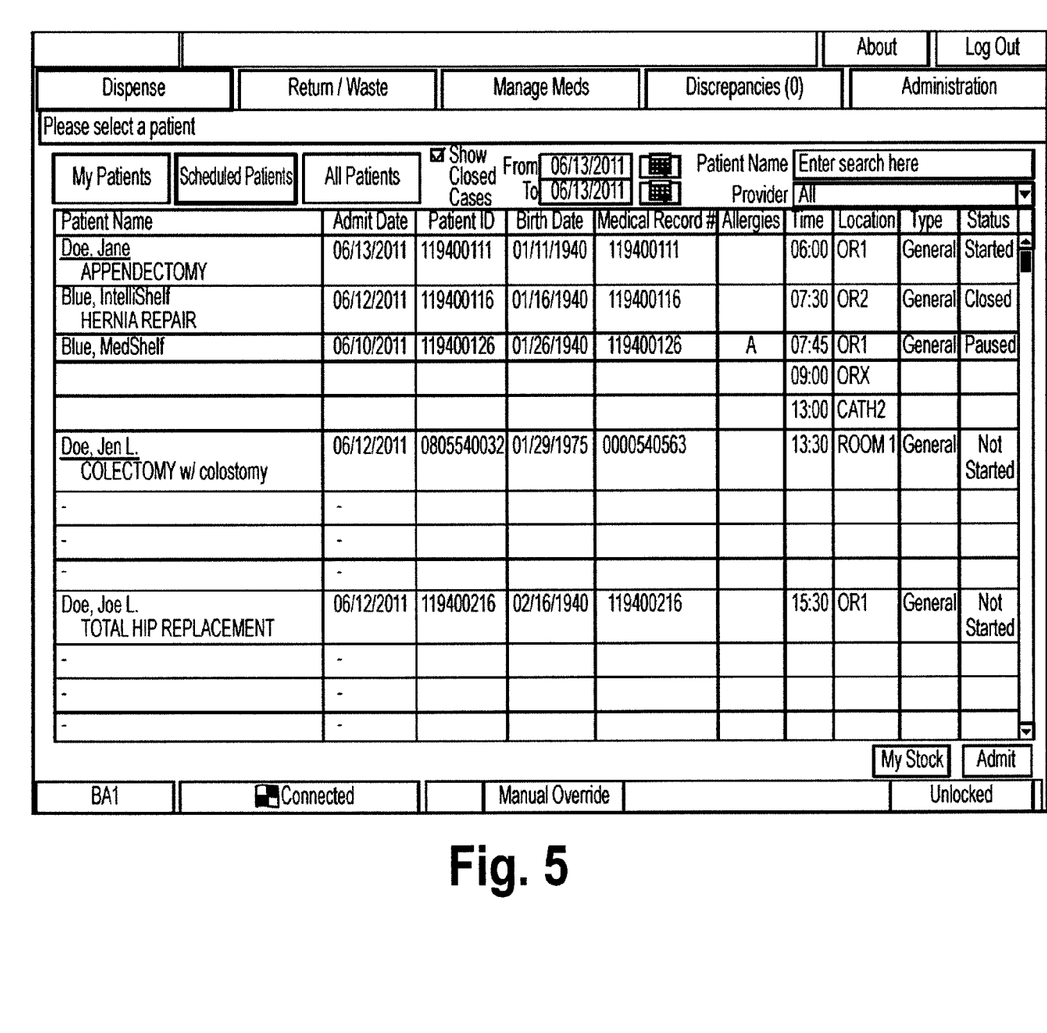
FIGS. 5-7 show exemplary input and output (including user interactions) that can be produced in accordance with various embodiments of the present invention.
Figure 6:
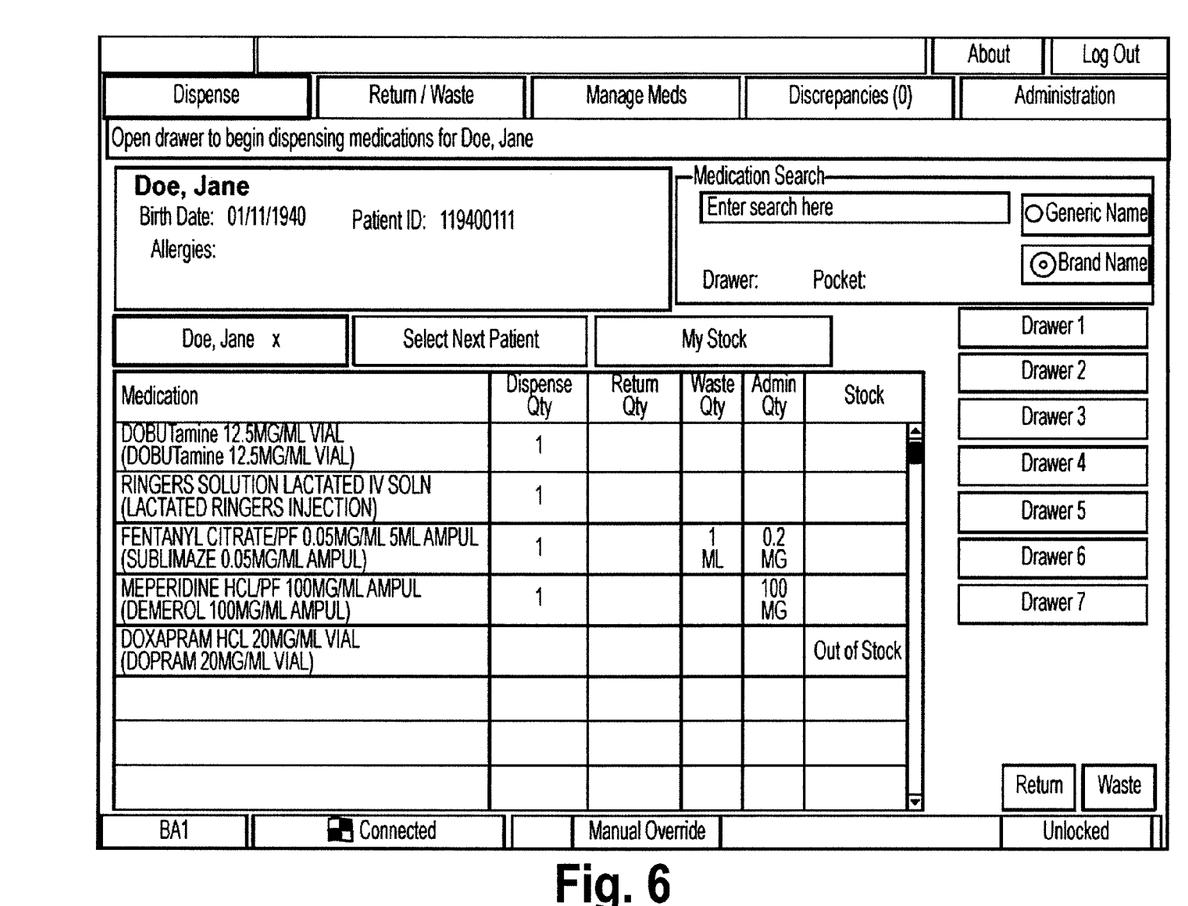
Figure 7:
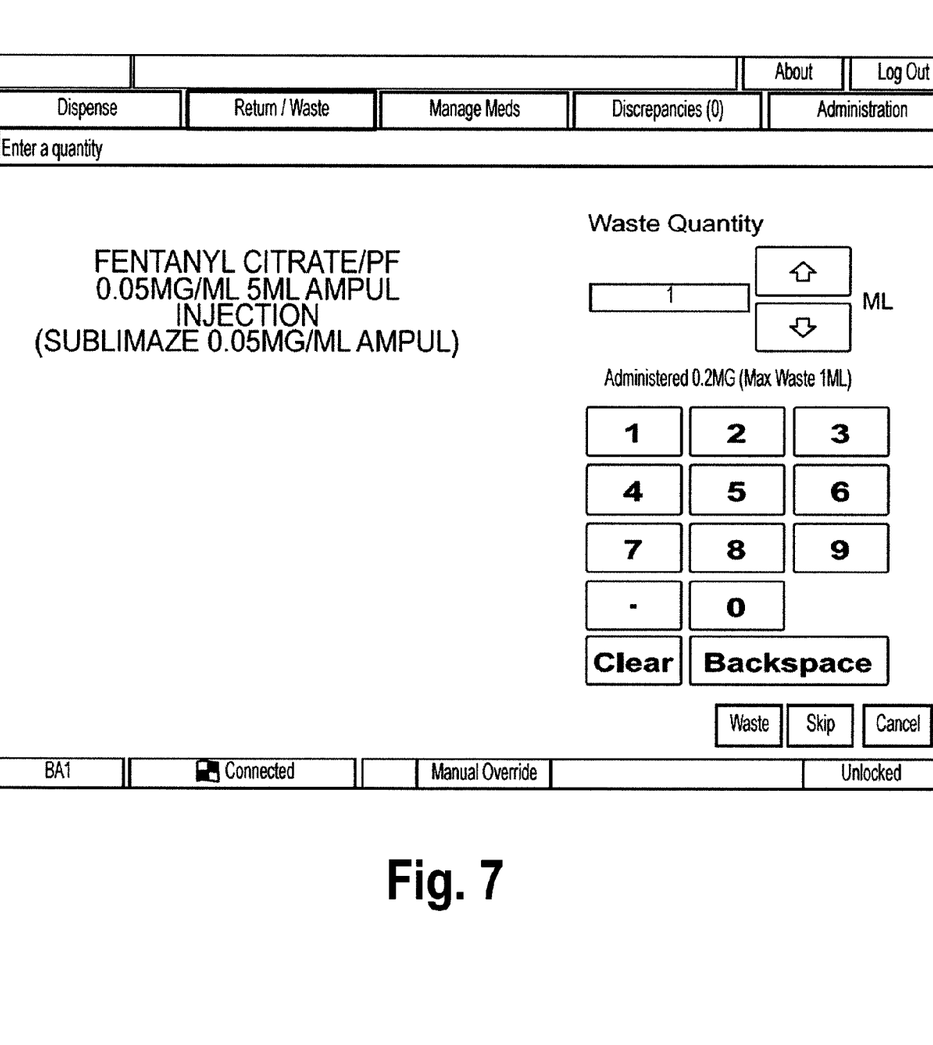

Reference will now be made to FIGS. 4-7. FIG. 4 provides a flowchart illustrating operations and processes that may be performed to track cases and medication inventory. FIGS. 5-7 show exemplary input and output (including user interactions) that can be produced in accordance with various embodiments of the present invention.

1. Cases and Medication Lists

In one embodiment, as indicated in Block 400 of FIG. 4, the process may begin with an appropriate computing entity (e.g., anesthesia care computing entity 100, data storage/facilitation computing entity 115) receiving (e.g., via the case module 270) one or more cases corresponding to patients. As will be recognized, a case may be a medical record, a part of a medical record associated with a specific medical provider, a record of a particular illness or health concern, a record of a medical procedure to be performed, and/or the like. In a particular embodiment, a case may at least identify a patient and a medical procedure to be performed for a patient, such as an appendectomy, a hernia repair, a hip replacement, a colectomy, and/or a variety of other medical procedures.

In one embodiment, as indicated in Block 405 of FIG. 4, an appropriate computing entity (e.g., anesthesia care computing entity 100) can cause display of the upcoming cases for a specific time period for a medical provider to view, select, and/or access. For example, the appropriate computing entity (e.g., anesthesia care computing entity 100) can cause display of the cases that are scheduled for pre-evaluation consultations for a given day or other time period. Thus, when a patient has a pre-evaluation consultation with a medical provider (e.g., anesthesiologist, resident assistant), the medical provider can select the appropriate case to access and input (e.g., via operation of an anesthesia care computing entity 100) patient information (e.g., medical data). For instance, the medical provider may input (and the appropriate computing entity receive) the patient's vitals, notes about the patient's medical history, known patient allergies, and/or the like. Also, in one embodiment, the medical provider (and/or the appropriate computing entity) can input, identify, associate, and/or create one or more anesthesia plans (including medication lists) for the patient's medical procedure (Block 410 of FIG. 4).

As indicated, in one embodiment, an anesthesia plan may include a medication list of medications (and corresponding quantities) that the medical provider would like (or is recommended or required to have) available for use before, during, and/or after the patient's medical procedure. To do so, in one embodiment, the medical provider may access, for example, facility guidelines or national guidelines identifying medications that should be used for certain medical procedures. In one embodiment, each medical procedure (e.g., appendectomy, hernia repair, hip replacement, colectomy) may have a suggested or required medication list. For example, the medication list in an anesthesia plan for an appendectomy may indicate that (1) Tamine, (2) Fentanyl Citrate, (3) Demerol, and (4) Dopram should be available for use before, during, and/or after the medical procedure. Further, the medication list in an anesthesia plan may be more specific. For example, the medication list in an anesthesia plan for an appendectomy may indicate that (1) four 12 mg vials of Tamine, (2) two 5 ml ampules of Fentanyl Citrate, (3) two 100 mg ampules of Demerol, and (4) two 20 mg vials of Dopram should be available for use before, during, and/or after the medical procedure.

In another embodiment, the anesthesia plan may be based on and/or adapted to the medical provider's preferences, patient allergies, and/or the like.

In one embodiment, after or as a result of the pre-evaluation consultation, the appropriate computing entity (e.g., anesthesia care computing entity 100, data storage/facilitation computing entity 115) can then update the case to reflect the patient information, anesthesia plan, and/or medication list (Blocks 415 of FIG. 4). Alternatively or additionally, this may also include updating the patient's medical record with corresponding information (e.g., medical data). The appropriate computing entity (e.g., data storage/facilitation computing entity 115) can then make the case or medical record (including the corresponding anesthesia plan and medication list) available to various other computing entities (Block 420 of FIG. 4).

In one embodiment, the patient information, anesthesia plan, and/or medication list can facilitate the update of (or creation of) one or more medication dispense queues. A medication dispense queue may be an electronic record of medications and quantities (e.g., an electronic record of one or more medication lists) associated with a facility, a surgical/procedural area, a medication dispensing unit 110, and/or a case. For instance, a medication dispense queue can be created for each patient's case, e.g., identifying all the medications and quantities (e.g., dosages) that should be available for use before, during, and/or after the patient's medical procedure. For example, FIG. 5 shows that Joe L. Doe is scheduled for a total hip replacement surgery, Jane Doe is scheduled for an appendectomy, and Jen L. Doe is scheduled for a colectomy with a colostomy. Thus, each of these cases may each be associated with a medication dispense queue (e.g., an electronic record of one or more medication lists).

In one embodiment, when the surgical/procedural area scheduled to be used for the medical procedures is finalized, the medication dispense queues (e.g., medication lists) associated with the patients, cases, and/or medical procedures can be provided to the appropriate medication dispensing unit 110. That is, each medication dispensing unit 110 may have a medication dispense queue (e.g., medication list). A medication dispense queue for a medication dispensing unit 110 may include all medication and quantities that should be stocked on the medication dispensing unit 110 for a given medical procedure or for a given time period (e.g., including multiple medical procedures). In such an embodiment, a medication dispensing unit 110 may be associated with (a) a single medication dispense queue for all cases for a given day or (b) multiple medication dispense queues, each corresponding to a specific case.

Continuing with the above example, assuming Joe, Jen, and Jane are all scheduled to have their medical procedures performed in surgical/procedural area 11 at Northside Hospital, the medication dispensing unit 110 located in surgical/procedural area 11 at Northside Hospital may have one or more medication dispense queues created or updated that identify all the medications and quantities that should be available for the three separate medical procedures. This queuing of medications can be used to ensure that the medication dispensing units 110 are sufficiently stocked with the medications that should be available for a specific procedure or for all the procedures that are scheduled to be performed with the aid of a specific medication dispensing unit 110 on a particular day (or other time period).

2. Stocking of Medication Dispensing Units (MDU)

In one embodiment, when a surgical/procedural area schedule (or other schedule) is finalized for a given day (or other time period), the appropriate computing entity (e.g., data storage/facilitation computing entity 115, MDU computing entity 300) can identify one or more medication dispense queues for a surgical/procedural area, a medication dispensing unit 110, and/or a case. For example, each night or morning before the start of scheduled medical procedures, the appropriate computing entity (e.g., data storage/facilitation computing entity 115, MDU computing entity 300) can determine (e.g., monitor) whether the medication dispensing units 110 that will be used for upcoming medical procedures are stocked with (e.g., housing) all of the medications and respective quantities identified in the medication dispense queue or queues (Blocks 425, 435). Such a determination may be performed regularly, periodically, and/or continuously to monitor the inventory (e.g., medication and supplies) with which the medication dispensing units 110 are stocked (e.g., is housing).

In one embodiment, after determining that a medication dispensing unit 110 is not stocked with (e.g., housing) each of the medications and the respective quantities identified in the medication dispense queue or queues (Blocks 425, 435), the appropriate computing entity (e.g., data storage/facilitation computing entity 115) can generate a stocking order to provide the proper medications identified in the medication dispense queue or queues to the appropriate medication dispensing units 110 before the scheduled medical procedure or procedures (Block 430 of FIG. 4). In another embodiment, the appropriate computing entity (e.g., data storage/facilitation computing entity 115) can also generate a stocking order if the inventory of medications is low or anticipated that the medications might be used before the medical procedure. Such stocking orders can be generated on a regular, periodic, and/or continuous basis. In one embodiment, this approach can also provide an opportunity to remove any unnecessary medications (e.g., medications not identified in a queue) from a medication dispensing unit 110.

In one embodiment, stocking orders can be sent to a variety of computing entities, including a pharmacy computing entity. With a stocking order, pharmacy personnel and pharmacy computing entities can take appropriate measures to ensure that the medication dispensing unit 110 is stocked with the medications (and quantities) identified in the medication dispense queue or queues. Additionally, pharmacy personnel and pharmacy computing entities can manage medication inventories based on upcoming medical procedures, historical usage, trends, and/or the like. In various embodiments, these approaches can be used to minimize out of stock occurrences experienced by medical providers. Moreover, by accurately understanding medication needs, pharmacy personnel and pharmacy computing entities, for example, can proactively determine medications and quantities that need to be stocked and thereby reduce excess inventory while supporting patient needs. Accordingly, when the scheduled time arrives for a medical provider to perform one or more medical procedures, the medication dispensing unit 110 that will be used can be pre-stocked with all the necessary medications and quantities (e.g., dosages).

3. Tracking of Medications

In one embodiment, a surgical/procedural area (or other similar facility), for example, for performing medical procedures may include one or more anesthesia care computing entities 100 and one or more medication dispensing units with MDU computing entities 300. In this embodiment, such entities may be in communication with one or more data storage/facilitation computing entities 115. In another embodiment, a surgical/procedural area may include one or more medication dispensing units with MDU computing entities 300. In this embodiment, such entities may also be in communication with one or more data storage/facilitation computing entities 115 and/or one or more anesthesia care computing entities 100. Thus, although the following example describes an embodiment using both an anesthesia care computing entity 100 and an MDU computing entity 300 in a surgical/procedural area, such an architecture is provided for illustrative purposes and is not limiting to embodiments of the present invention.

As indicated, when the scheduled time arrives for a medical provider to perform one or more medical procedures, one or more medication dispensing units 110 that will be used for the procedure can be pre-stocked in accordance with one or more medication dispense queues (e.g., one or more medication lists). Further, as shown FIG. 5, the cases scheduled for a particular time period (e.g., day) can be displayed by the appropriate computing entity (e.g., both the anesthesia care computing entity 100 and the MDU computing entity 300) for medical providers to view or select, for example (Blocks 440, 445 of FIG. 4). Then, as indicated in Blocks 450, 455 of FIG. 4, a medical provider can select a particular case and/or patient via the appropriate computing entity (e.g., anesthesia care computing entity 100, MDU computing entity 300). Continuing with the above example, the medical provider (e.g., anesthesiologist, resident assistant) can select Jane Doe's case for the appendectomy. That is, in one embodiment, the medical provider (e.g., anesthesiologist, resident assistant) can select (and the appropriate computing entity receive) Jane Doe's case via both the anesthesia care computing entity 100 and the MDU computing entity 300.

In one embodiment, selection of the case via the anesthesia care computing entity 100 can initiate tracking by the anesthesia care computing entity 100 of the medications that are dispensed, administered, unused, returned, and/or wasted (Block 460 of FIG. 4). Similarly, selection of the case via the MDU computing entity 300 can cause display of the medication dispense queue (e.g., medication list for the patient's medical procedure) for the selected case, shown in FIG. 6 (Block 465 of FIG. 4). And, such a selection can initiate tracking by the MDU computing entity 300 of the medications that are dispensed, administered, unused, returned, and/or wasted.

In one embodiment, when a medication is dispensed, an appropriate computing entity (e.g., anesthesia care computing entity 100, data storage/facilitation computing entity 115, MDU computing entity 300) can receive a notification that a medication of a particular quantity has been dispensed (e.g., removed) from a medication dispensing unit 110 (Block 470 of FIG. 4). For example, in one embodiment, such notifications can be automatically generated when a medical provider (e.g., anesthesiologist or resident assistant) dispenses (e.g., removes) a medication of a particular quantity from a medication dispensing unit 100. Exemplary processes for such automatic detections and notifications are described in U.S. patent application Ser. No. 12/041,800, which is hereby incorporated in its entirety by reference. As described in the incorporated patent application, such automatic detection techniques include using optical sensors (and any corresponding circuitry), mechanical switch sensors (and any corresponding circuitry), and/or reflective sensors (and any corresponding circuitry) to detect the dispensing (e.g., removal) of medication. In another embodiment, the medical provider (e.g., anesthesiologist or resident assistant) can generate notifications by manually inputting the medication and quantity that was removed from the medication dispensing unit 110. Such manual input may include, for example, selecting (e.g., via a keyboard, mouse, and/or touchscreen) a medication from a displayed list. In another embodiment, the manual input may include scanning a barcode (or other code) or interrogating an RFID tag attached or corresponding to a medication. In one embodiment, this approach allows for an appropriate computing entity (e.g., anesthesia care computing entity 100, data storage/facilitation computing entity 115, MDU computing entity 300) to regularly, periodically, and/or continuously monitor the inventory (e.g., medication and supplies) with which the medication dispensing units 110 are stocked (e.g., are housing). As will be recognized, a variety of other approaches and techniques may also be used to adapt to various needs and circumstances to generate notifications for dispensed medications.

In one embodiment, an appropriate computing entity (e.g., anesthesia care computing entity 100, MDU computing entity 300) may implement one or more confirmation measures (e.g., sometimes require multiple medical providers to confirm) in response to notification that a medication has been dispensed (e.g., removed) from a medication dispensing unit 110. For example, via a display, the appropriate computing entity (e.g., anesthesia care computing entity 100, MDU computing entity 300) may cause display of information regarding the medication that was dispensed. For instance, the display may provide text that reads "A 20 mg vial of Dopram was dispensed." In one embodiment, the display (e.g., a touch screen) may also prompt the medical provider to input a confirmation that she dispensed the identified medication. As will be recognized, a variety of other approaches and techniques may also be used to adapt to various needs and circumstances.

In one embodiment, an appropriate computing entity (e.g., anesthesia care computing entity 100, data storage/facilitation computing entity 115, MDU computing entity 300) can receive a notification that a medication of a particular quantity has been returned to a medication dispensing unit 110 (Block 475 of FIG. 4). For example, as described above with respect to dispensed medications, such notifications can be automatically generated when a medical provider (e.g., anesthesiologist or resident assistant) returns a medication of a particular quantity to a medication dispensing unit 100. Moreover, the medical provider (e.g., anesthesiologist or resident assistant) can generate the notification by manually inputting (e.g., via keyboard, touchscreen, scanning, interrogating) the medication and quantity that was returned to the medication dispensing unit 110. In one embodiment, this approach allows for an appropriate computing entity (e.g., anesthesia care computing entity 100, data storage/facilitation computing entity 115, MDU computing entity 300) to regularly, periodically, and/or continuously monitor the inventory (e.g., medication and supplies) with which the medication dispensing units 110 are stocked (e.g., are housing). As will be recognized, a variety of other approaches and techniques may also be used to adapt to various needs and circumstances.

In one embodiment, an appropriate computing entity (e.g., anesthesia care computing entity 100, MDU computing entity 300) may implement one or more confirmation measures (e.g., sometimes require multiple medical providers to confirm) in response to notification that a medication has been returned to a medication dispensing unit 110. For example, via a display, the appropriate computing entity (e.g., anesthesia care computing entity 100, MDU computing entity 300) may cause display of information regarding the medication that was returned. For example, the display may provide text that reads "A 20 mg vial of Dopram was returned." In one embodiment, the display (e.g., a touch screen) may also prompt the medical provider to input a confirmation that she returned the identified medication.

In one embodiment, an appropriate computing entity (e.g., anesthesia care computing entity 100, MDU computing entity 300) can also receive notification that a medication of a particular quantity has been administered to a patient (Block 480 of FIG. 4). For example, in one embodiment, a medical provider (e.g., anesthesiologist or resident assistant) can manually input via the appropriate computing entity (e.g., anesthesia care computing entity 100, MDU computing entity 300) a medication and quantity that was administered to a patient. For example, after dispensing a 20 mg vial of Dopram from a medication dispensing unit 120, the medical provider (e.g., anesthesiologist or resident assistant) may administer only a portion of the 20 mg, such as 10 mg. In this example, the medical provider may manually input via the appropriate computing entity (e.g., anesthesia care computing entity 100, MDU computing entity 300) that she administered 10 mg of Dopram to the patient Jane Doe.

In one embodiment, the appropriate computing entity (e.g., anesthesia care computing entity 100, data storage/facilitation computing entity 115, MDU computing entity 300) may also implement one or more confirmation measures (e.g., sometimes require multiple medical providers to confirm) in response to notification that a medication has been administered to a patient. For example, via a display, the appropriate computing entity (e.g., anesthesia care computing entity 100, MDU computing entity 300) may cause display of information regarding the medication that was administered. For example, the display may provide text that reads "You administered 10 mg of Dopram to Jane Doe at 10:24 am." In one embodiment, the display may also prompt the medical provider to input a confirmation that she administered the identified medication and quantity. As will be recognized, a variety of other approaches and techniques may also be used to adapt to various needs and circumstances.

In one embodiment, an appropriate computing entity (e.g., anesthesia care computing entity 100, MDU computing entity 300) can also receive notification that a medication of a particular quantity has been wasted (e.g., properly disposed of in a biohazard return bin), as indicated in Block 475 of FIG. 4. For example, in one embodiment, such notifications can be generated by manual input from a medical provider (e.g., anesthesiologist or resident assistant). By way of example, a medical provider may dispense a 20 mg vial of Dopram, but only administer 10 mg to the patient. In such a case, the remaining 10 mg of Dopram can be wasted (e.g., properly disposed of in a biohazard return bin). The medical provider can then input to an appropriate computing entity (e.g., anesthesia care computing entity 100, MDU computing entity 300) that the remaining 10 mg of Dopram was wasted (e.g., properly disposed of in a biohazard return bin), as shown in FIG. 7. In one embodiment, this approach allows for an appropriate computing entity (e.g., anesthesia care computing entity 100, data storage/facilitation computing entity 115, MDU computing entity 300) to regularly, periodically, and/or continuously monitor the inventory (e.g., medication and supplies) with which the medication dispensing units 110 are stocked (e.g., are housing).

In one embodiment, the above processes, operations, generations, notifications, and/or input can take place before, during, and/or after a medical procedure for each medication dispensed, administered, returned, and/or wasted. In various embodiments, these approaches allow the appropriate computing entities (e.g., anesthesia care computing entity 100, MDU computing entity 300) to monitor and track the medications for each case and/or for a given time period.

In one embodiment, when the medical procedure has been completed, the appropriate computing entity (e.g., anesthesia care computing entity 100, MDU computing entity 300) can receive input closing the case (Block 490 of FIG. 4). Closing a case may indicate that a medical procedure has been completed and therefore trigger (e.g., via the reconciliation module 260) the appropriate computing entity to account for all medications in the medication dispense queue and/or the medication dispensing unit 110. Accounting for all the medications may include identifying all medications and quantities that have been dispensed, returned, administered, returned, wasted, and/or unused. This accounting also allows for the appropriate computing entity (e.g., anesthesia care computing entity 100, MDU computing entity 300) to determine whether any medications or quantities are unaccounted for based on the history of what medications have been dispensed, returned, administered, returned, wasted, and/or unused.

In one embodiment, for any medications and quantities that have been dispensed, but otherwise unaccounted for (e.g., not recorded as being returned, administered, wasted, and/or unused), the appropriate computing entity (e.g., anesthesia care computing entity 100, MDU computing entity 300) can generate a perceivable alert (e.g., sound, message, text, etc.) to the medical provider (Blocks 490, 485 of FIG. 4). For example, via a display, the appropriate computing entity (e.g., anesthesia care computing entity 100, MDU computing entity 300) may cause display of text regarding a medication that is unaccounted for: "You dispensed 20 mg of Dopram and only administered 10 mg of Dopram to Jane Doe. Please account for the other 10 mg." In one embodiment, the appropriate computing entity (e.g., anesthesia care computing entity 100, MDU computing entity 300) may require the medical provider to account for any unaccounted for medications and quantities before a case can be closed.

In another embodiment, an appropriate computing entity (e.g., anesthesia care computing entity 100, MDU computing entity 300) can prepopulate medications and quantities that have been returned or wasted by the difference of the quantity dispensed and the quantity administered. In this embodiment, the appropriate computing entity (e.g., anesthesia care computing entity 100, MDU computing entity 300) may cause display of text regarding the prepopulated information: "You dispensed 20 mg of Dopram and only administered 10 mg of Dopram to Jane Doe. The remaining 10 mg was wasted. Please confirm." Such a process can be used to eliminate duplicate entry for selecting medications, which can save medical providers (e.g., anesthesiologist, resident assistant) time.

In one embodiment, various reports can be generated (e.g., via the reporting module 250) regarding cases, patients, and medical dispensing units 110. For example, the appropriate computing entity (e.g., anesthesia care computing entity 100, MDU computing entity 300, data storage/facilitation computing entity 115) can generate reports of the medications and quantities that were dispensed, administered, unused, returned, and/or wasted (and identify the corresponding times).

In embodiment, such reports can identify the medications and quantities remaining on the medication dispensing unit 110. Using this information and/or from regularly, periodically, and/or continuously monitoring the inventory, the appropriate computing entity (e.g., data storage/facilitation computing entity 115, MDU computing entity 300) can determine (e.g., monitor) whether the medication dispensing unit 110 is stocked with (e.g., housing) each of the medications and the respective quantities remaining in the medication dispense queue or queues (Blocks 425, 495). For example, after Jane's medical procedure, the appropriate computing entity (e.g., data storage/facilitation computing entity 115, MDU computing entity 300) can determine whether the medication dispensing unit 110 is stocked with the medications (and supplies) in the medication dispense queues for Joe and Jen.

In one embodiment, after determining that a medication dispensing unit 110 is not stocked with (e.g., housing) each of the medications and the respective quantities remaining in the medication dispense queue or queues (Blocks 425, 435), the appropriate computing entity (e.g., data storage/facilitation computing entity 115) can generate a stocking order to provide the proper medications (Block 430 of FIG. 4). As previously described, the stocking order can be sent to a variety of computing entities include a pharmacy computing entity. With a stocking order, pharmacy personnel and pharmacy computing entities can take appropriate measures to ensure that the medication dispensing unit 110 is stocked with the medications (and quantities) identified in the remaining medication dispense queue or queues. In various embodiments, these approaches can be used to proactively determine medications and quantities that need to be stocked and thereby reduce excess inventory while supporting patient needs.

In one embodiment, after a case has been closed, the appropriate computing entity (e.g., data storage/facilitation computing entity 115) can update the patient's medical record to reflect the medical procedure and any administered medications, along with the corresponding quantities (e.g., dosages) and administration times. This can provide a variety of providers and entities with a record of a patient's medical procedure.

III. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for medication management, the method comprising:
   identifying, via one or more processors, a case associated with a patient, wherein the case identifies a medical procedure to be performed for the patient;
   generating, via the one or more processors, a medication list for the medical procedure to be performed for the patient, wherein the medication list identifies a plurality of medications for potential use during the medical procedure to be performed for the patient;
   prior to the medical procedure, determining, via the one or more processors, whether a medication dispensing unit is stocked with each of the plurality of medications identified in the medication list for potential use during the medical procedure to be performed for the patient;
   after determining that the medication dispensing unit is not stocked with at least one of the plurality of medications identified in the medication list, generating, via the one or more processors, a stocking order to provide the at least one of the of the plurality of medications in the medication list to the medication dispensing unit for the medical procedure;
   receiving, via the one or more processors, notification that a quantity of a first medication from the medication list was dispensed from the medication dispensing unit during the medical procedure;
   receiving, via the one or more processors, notification that a quantity of the first medication was administered to the patient during the medical procedure; and
   determining, via the one or more processors, whether a quantity of the first medication that was dispensed from the medication dispensing unit is unaccounted for based at least in part on the quantity of the first medication that was administered to the patient.

2. The method of claim 1 further comprising, after determining whether a quantity of the first medication that was dispensed from the medication dispensing unit is unaccounted for, generating an alert.

3. The method of claim 1 further comprising:
   generating a report of (A) medications that were used during the medical procedure and (B) medications that were not used during the medical procedure; and
   generating a stocking order based at least in part on the report of the medications that were used during the medical procedure.

4. The method of claim 3, wherein the medications that were used are selected from the group consisting of administered medication and wasted medication.

5. The method of claim 4, wherein the medications that were not used are selected from the group consisting of unused medication and returned medication.

6. A computer program product for medication management, the computer program product comprising at least one non-transitory computer-readable storage medium having computer-readable program code portions stored therein, the computer-readable program code portions comprising:
- an executable portion configured to identify a case associated with a patient, wherein the case identifies a medical procedure to be performed for the patient;
- an executable portion configured to generate a medication list for the medical procedure to be performed for the patient, wherein the medication list identifies a plurality of medications for potential use during the medical procedure to be performed for the patient;
- an executable portion configured to, prior to the medical procedure, determine whether a medication dispensing unit is stocked with each of the plurality of medications identified in the medication list for potential use during the medical procedure to be performed for the patient;
- an executable portion configured to, after determining that the medication dispensing unit is not stocked with at least one of the plurality of medications identified in the medication list, generate a stocking order to provide the at least one of the of the plurality of medications in the medication list to the medication dispensing unit for the medical procedure;
- an executable portion configured to receive notification that a quantity of a first medication from the medication list was dispensed from the medication dispensing unit;
- an executable portion configured to receive notification that a quantity of the first medication was administered to the patient; and
- an executable portion configured to determine whether a quantity of the first medication that was dispensed from the medication dispensing unit is unaccounted for based at least in part on the quantity of the first medication that was administered to the patient.

7. The computer program product of claim 6 further comprising an executable portion configured to, after determining whether a quantity of the first medication that was dispensed from the medication dispensing unit is unaccounted for, generate an alert.

8. The computer program product of claim 6 further comprising:
- an executable portion configured to generate a report of (A) medications that were used during the medical procedure and (B) medications that were not used during the medical procedure; and
- an executable portion configured to generate a stocking order based at least in part on the report of the medications that were used during the medical procedure.

9. The computer program product of claim 6, wherein the medications that were used are selected from the group consisting of administered medication and wasted medication.

10. The computer program product of claim 9, wherein the medications that were not used are selected from the group consisting of unused medication and returned medication.

11. A system comprising one or more processors and one or more memory storage areas including computer program code, wherein the system is configured to:
- identify a case associated with a patient, wherein the case identifies a medical procedure to be performed for the patient;
- generate a medication list for the medical procedure to be performed for the patient, wherein the medication list identifies a plurality of medications for potential use during the medical procedure to be performed for the patient;
- prior to the medical procedure, determine whether a medication dispensing unit is stocked with each of the plurality of medications identified in the medication list for potential use during the medical procedure to be performed for the patient;
- after determining that the medication dispensing unit is not stocked with at least one of the plurality of medications identified in the medication list, generate a stocking order to provide the at least one of the of the plurality of medications in the medication list to the medication dispensing unit for the medical procedure;
- receive notification that a quantity of a first medication from the medication list was dispensed from the medication dispensing unit;
- receive notification that a quantity of the first medication was administered to the patient; and
- determine whether a quantity of the first medication that was dispensed from the medication dispensing unit is unaccounted for based at least in part on the quantity of the first medication that was administered to the patient.

12. The system of claim 11, wherein the system is further configured to, after determining whether a quantity of the first medication that was dispensed from the medication dispensing unit is unaccounted for, generate an alert.

13. The system of claim 11, wherein the system is further configured to:
- generate a report of (A) medications that were used during the medical procedure and (B) medications that were not used during the medical procedure; and
- generate a stocking order based at least in part on the report of the medications that were used during the medical procedure.

14. The system of claim 11, wherein the medications that were used are selected from the group consisting of administered medication and wasted medication.

15. The system of claim 14, wherein the medications that were not used are selected from the group consisting of unused medication and returned medication.

* * * * *